US00PP35203P2

(12) United States Plant Patent
Juneau

(10) Patent No.: US PP35,203 P2
(45) Date of Patent: Jun. 6, 2023

(54) GRAPEVINE PLANT NAMED 'JUNEAU BLANC'

(50) Latin Name: ***Vitis* hybrid**
Varietal Denomination: Juneau blanc

(71) Applicant: Ronald Juneau, Pont-Rouge (CA)

(72) Inventor: Ronald Juneau, Pont-Rouge (CA)

( * ) Notice: Subject to any disclaimer, the term of this patent is extended or adjusted under 35 U.S.C. 154(b) by 0 days.

(21) Appl. No.: 17/991,529

(22) Filed: Nov. 21, 2022

(30) Foreign Application Priority Data

Nov. 26, 2021 (CA) ..... PBR CA 2110765

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./207
CPC ..... A01H 6/88; A01H 5/08
See application file for complete search history.

*Primary Examiner* — Keith O. Robinson
(74) *Attorney, Agent, or Firm* — Penny J. Aguirre

(57) ABSTRACT

The invention is a new and distinct variety of Grapes plant named 'Juneau blanc' that is characterized by its good cold hardiness in Québec, Canada, its grapes that have thick skins and are resistant to fall frost, its vigorous growth habit with high fruit production, its grapes that are golden yellow in color at full maturity, its good disease resistance, its upward growing canes, and its juicy grapes with a fruity taste that are rich in aroma.

3 Drawing Sheets

Botanical classification: *Vitis* hybrid.
Variety denomination: 'Juneau blanc'.

CROSS-REFERENCE TO A RELATED APPLICATION

This application claims priority to a Canadian plant breeders' rights application filed on Nov. 26, 2021, application No. 21-10765, under 35 U.S.C. 119(f), the entire contents of which is incorporated by reference herein.

BACKGROUND OF THE INVENTION

The present invention relates to a new and distinct cultivar of grapevine plant botanically of hybrid origin and known as *Vitis* 'Juneau blanc', referred to hereafter by its cultivar name, 'Juneau blanc'.

The new cultivar was derived from a controlled breeding program conducted by the Inventor in Portneuf County, Québec, Canada. The goal of the breeding program is to develop new cold hardy grape varieties with reliable winter hardiness in Québec, Canada combined with good characteristics for winemaking.

The new cultivar arose from a cross made in 1990 between an unnamed and unpatented proprietary plant in the Inventor's breeding program, reference no. "E.S.2-3-17" as the female parent and *Vitis* 'Chenin blanc' (not patented) as the male parent. The new *Vitis* was selected as a single unique plant in 2011 from the resulting seedlings.

Asexual propagation of the new cultivar was first accomplished by hardwood stem cuttings in 2012 by the Inventor in St-Ubalde, Québec, Canada. Asexual propagation of the new cultivar by hardwood stem cuttings and tissue culture using meristematic tissue has determined that the characteristics are stable and true to type in successive generations.

SUMMARY OF THE INVENTION

The following traits have been repeatedly observed and represent the characteristics of the new cultivar. These attributes in combination distinguish 'Juneau blanc' as a new and unique cultivar of *Vitis*.

1. 'Juneau blanc' exhibits dense grape clusters with shoulders.
2. 'Juneau blanc' exhibits good cold hardiness in Québec, Canada.
3. 'Juneau blanc' exhibits grapes that have thick skins and are resistant to fall frost.
4. 'Juneau blanc' exhibits a vigorous growth habit with high fruit production.
5. 'Juneau blanc' exhibits grapes that are golden yellow in color at full maturity.
6. 'Juneau blanc' exhibits good disease resistance.
7. 'Juneau blanc' exhibits upward growing canes.
8. 'Juneau blanc' exhibits juicy grapes with a fruity taste that are rich in aroma.

The female parent plant of 'Juneau blanc' differs from 'Juneau blanc' in having a less vigorous habit, an earlier maturity date, and grape clusters that are smaller in size with less weight per cluster. The male parent plant of 'Juneau blanc' differs from 'Juneau blanc' in having much less cold hardiness, less resistance to disease, and a later grape maturity date. 'Juneau blanc' can also be compared to the *Vitis* cultivars 'Adalmiina' (not patented) and 'Jhenin blanc' (not patented). 'Adalmiina' is similar to 'Juneau blanc' in fruit skin color. 'Adalmiina' differs from 'Juneau blanc' in having leaves, vine buds, and young shoots that are different in shape and appearance and grapes that have a different flavor with skins that are less thick. 'Jhenin blanc' is similar to 'Juneau blanc' in fruit skin color at maturity and in having grape clusters and berries that are similar in shape. 'Chenin blanc' differs from 'Juneau blanc' in having grapes that do not reach maturity in in Québec, Canada and in being less cold hardy.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include a website listing by Vinifera Rustique.

BRIEF DESCRIPTION OF THE DRAWINGS

The accompanying color photographs illustrate the overall appearance and distinct characteristics of the new grape cultivar. The photographs were taken of plants about 6 years in age of the new cultivar as grown outdoors in a field in Saint-Ubalde, Québec, Canada.

The photograph in FIG. 1 provides a side view of the plant habit of 'Juneau blanc' with fruit.

Figure 1:
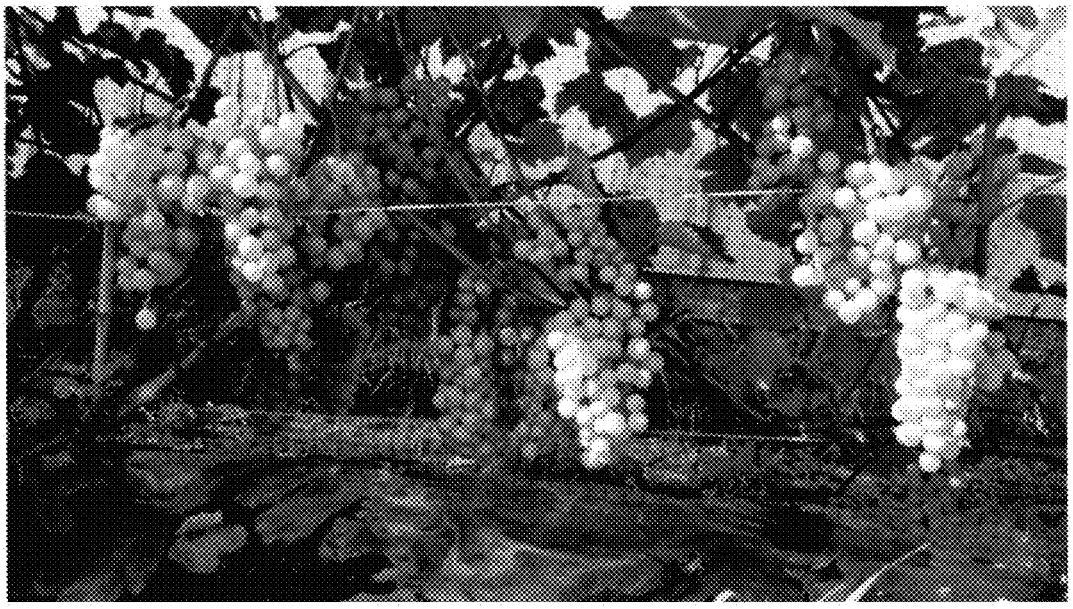
Figure 2:
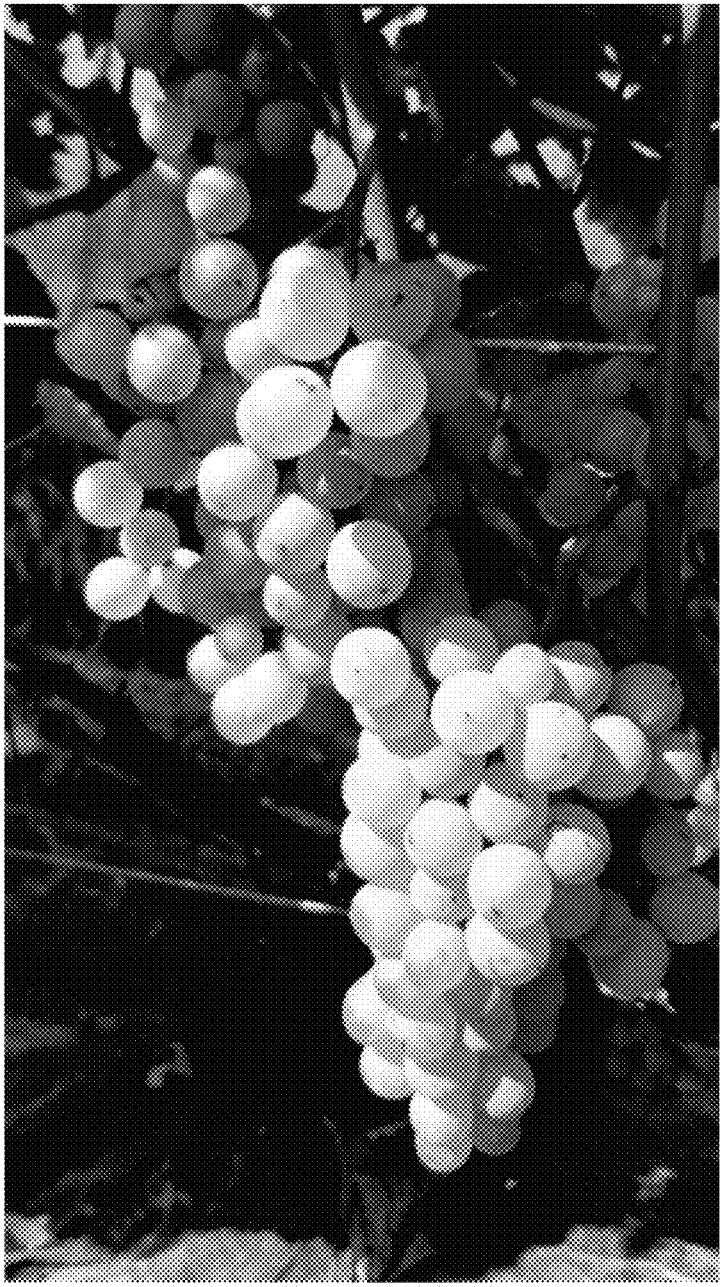

The photograph in FIG. 2 provides a close-up view of the fruit of 'Juneau blanc'.

Figure 3:
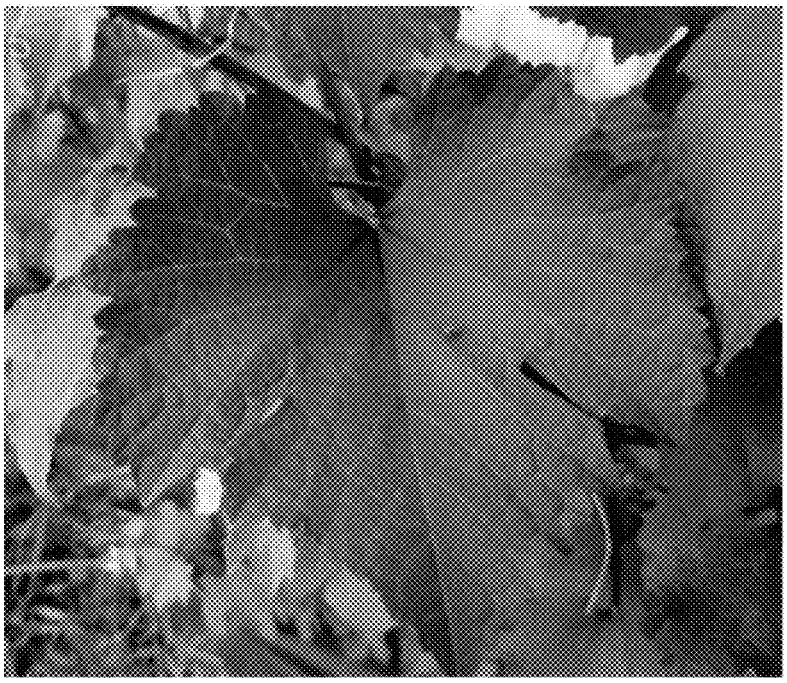

The photograph in FIG. 3 provides a close-up view of the upper leaf surface of 'Juneau blanc'.

Figure 4:
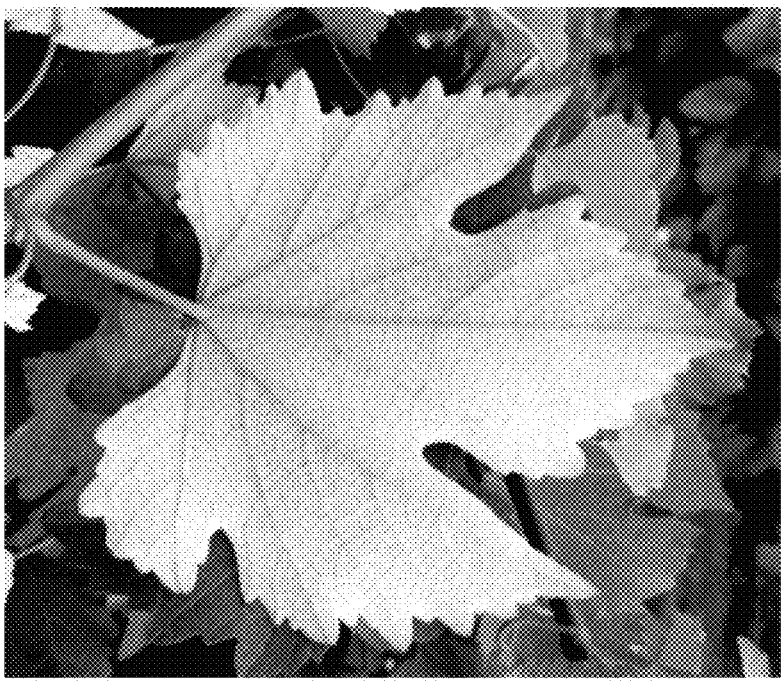

The photograph in FIG. 4 provides a close-up view of the lower leaf surface of 'Juneau blanc'.

The colors in the photographs are as close as possible with digital photography techniques available, the color values cited in the detailed botanical description accurately describe the colors of the new cultivar of grape.

DETAILED BOTANICAL DESCRIPTION OF THE PLANT

The following is a detailed description of plants six years in age as grown outdoors in a trial field in Saint-Ubalde, Québec, Canada. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Typically commences blooms about June 26th in Pontneuf County, Québec, Canada.
*Plant type.*—Perennial fruit producing vine.
*Plant habit.*—Open but orderly.
*Cold hardiness.*—At least to U.S.D.A. Zone 4a.
*Propagation.*—Hardwood stem cuttings and tissue culture.
*Root description.*—Fibrous and fine.
*Root development.*—An average of 21 days for root initiation with a young plant produced from a rooted cutting in 45 to 60 days.
*Growth rate.*—Vigorous.

Cane description:

*Color of canes.*—166B to 166C.
*Length of canes.*—1.2 m.
*Diameter of canes.*—1 cm.
*Internode length.*—12 cm.
*Lenticels.*—None observed.
*Cane cross-section shape.*—Round.
*Cane strength.*—Strong.
*Cane surface.*—Glabrous.
*Density of hairs on mature cane.*—None observed.
*Tendril pattern on shoot.*—2,0,2,0 etc. (two nodes with a tendril followed by one node without).
*Tendrils forked.*—Yes.
*Tendril texture.*—Glabrous.
*Tendril length.*—11 to 20 cm in length, 2 to 3 mm in width.
*Tendril color.*—On young shoots N144D to 145A, mature 144D to 178A.
*Bud width.*—2 mm.
*Bud length.*—5 mm.
*Bud shape.*—Triangular.
*Bud color.*—144B to 146D.
*Bud burst.*—Late.

Trunk description:

*Bark texture.*—Roughly striated.
*Bark color.*—N200A to 200C.
*Trunk diameter.*—An average of 4.5 cm on diameter measured 20 cm above soil on 6 year-old-trunk.

Leaf description:

*Length of blade.*—14.8 cm.
*Width of blade.*—13 cm.
*Shape of blade.*—Pentagonal to wedge-shaped.
*Leaf division.*—Simple.
*Leaf base.*—Cordate.
*Leaf apex.*—Acute.
*Leaf attachment.*—Petiolate.
*Leaf arrangement.*—Alternate.
*Number of lobes.*—5.
*Blade margins.*—Incised into lobes with lobes serrated.
*Length of primary (midrib) vein n1 from the tip of the blade to the petiole sinus.*—12.8 cm.
*Length of vein n2 from the tip of the first major lobe of the blade to the petiole sinus.*—11 cm.
*Length of vein n3 from the tip of the second major lobe of the blade to the petiole sinus.*—5.1 cm.
*Length of vein n4 from the tip of the third major lobe of the blade to where it joins the vein measured in n3.*—1.1 *cm.*
*Length of vein n5 from the tip of the first tooth proximal to the petiole sinus to where it joins the vein measured in n4.*—1.1 *cm.*
*Length of n2 teeth.*—0.75 cm.
*Width of n2 teeth.*—0.75 cm.
*Length/width ratio of n2 teeth.*—Small, 1:1.
*Length of n4 teeth.*—0.3 cm.
*Width of n4 teeth.*—0.4 cm.
*Length/width ratio of n4 teeth.*—Small, 1:1.
*Shape of teeth.*—Slightly convex.
*Shape of petiolar sinus.*—Wide open.
*Shape of base of petiolar sinus.*—Wide, u-shaped.
*Depth of petiolar sinus.*—2.5 cm.
*Width of petiolar sinus.*—3.9 cm.
*Petiole.*—12.3 cm in length, 2 to 3 mm in width.
*Shape of upper sinuses.*—Narrow v to u-shaped.
*Shape of base of upper sinuses.*—U-shaped.

*Pubescence on adaxial surface*.—None observed.
*Pubescence on abaxial surface*.—Dense hairs on veins, very dense pubescence between veins, erect hairs between veins absent.
*Color of adaxial leaf surface*.—A color between 143C and 144A.
*Color of abaxial leaf surface*.—144B to 144C.
*Color of leaf petiole*.—144A to 144B.
*Center lobe size*.—8 cm in length and 8.5 cm in width.
*Lateral lobe size*.—4.5 cm in length and 5 cm in width.
*Basal lobe size*.—2.4 cm in length and 2 cm in width.

Young shoot description:
*Form of shoot tip*.—Slightly to half open.
*Density of prostate hairs on tip*.—Absent.
*Density of erect hairs on tip*.—Absent.
*Petiole pigmentation*.—146A.
*Shoot attitude* (*aspect*).—Semi-erect.
*Shoot pigmentation* (*internodes and nodes*).—A blend of 180A on the ventral side and 144A on the dorsal side.
*Young leaves*.—146A on the upper surface, with a faint blush of 181B along the margin-edge tips of the upper lobes, and a blend of 146A to 146B on the lower surface.

Flower description:
*Fragrance*.—Slightly fragrant.
*Mean time of flowering*.—About June 26$^{th}$ in Portneuf County, Québec, Canada.
*Color of calyx*.—144A.
*Sepal number*.—5, sepals fused into continuous calyx.
*Calyx shape*.—Ring-shaped.
*Calyx size*.—Length; <1 mm in, width; 2 mm.
*Calyx apex*.—Fused to ovary.
*Calyx base*.—Fused to pedicel.
*Calyx persistence*.—Not persistent.
*Nectary*.—1.5 mm in diameter, <1 mm in length, 143C in color.
*Calyx surface*.—Glabrous on both surfaces.
*Petals*.—5, fused in calyptra cohering at summit; 2.5 mm in width and 1 mm in depth and separating at base; 4 mm in width, 2 mm in depth; reflexed after dehiscence, 144A in color on both surfaces, glabrous on both surfaces, margins entire.
*Inflorescence type*.—Cluster.
*Inflorescence lastingness*.—About 2 weeks.
*Cluster size*.—About 10 cm in length and 3.5 cm in width.
*Shape of cluster*.—Narrow to slightly conical, with 1 to 2 small shoulders.
*Number of flowers*.—Average of 115, 18 on shoulders if present.
*Flower buds*.—3 mm in length, 2 mm in width, 144A in color, oblanceolate in shape, oblanceolate in shape, glabrous surface.
*Flower size*.—4 mm in height, 1.5 cm in width (to end of stamens).
*Pollen fertility*.—Fertile based on use in controlled crosses.

Reproductive organs (fully developed stamens and fully developed gynoecium):
*Color of stamen*.—Anther; 4D, filament; 160C to 160D.
*Stamen number*.—Average of 5.
*Filament length*.—4 mm.
*Anther*.—1 mm in length.
*Pollen quantity and color*.—Abundant and 10C in color.
*Pistil*.—1, ovary; 1.5 mm in length, 1 mm in width at base, urn-shaped, glabrous surface, 144A in color, stigma; 1 mm in width and <1 mm in length, 154C in color.
*Pedicel*.—3.5 mm and <1 mm in width, surface glabrous, 144C in color.
*Peduncle*.—To base of cluster, varying between 2.5 cm and 3 to 4 mm in width, glossy surface, color; 144A suffused with 184B.

Fruit description:
*Cluster length*.—12.5 cm.
*Cluster diameter*.—7.6 cm.
*Cluster weight*.—131 g.
*Cluster number*.—Average of 2 per cane.
*Cluster density*.—Dense, average of 107 berries per cluster.
*Berry weight*.—2.6 g.
*Berry length*.—1.7 cm.
*Berry diameter at equator*.—1.7 cm.
*Berry shape*.—Round.
*Berry cross-section*.—Circular (symmetrical).
*Berry skin thickness*.—Thick.
*Berry, color of skin*.—A blend of 153D and 154A to 154B.
*Berry, color of flesh*.—157A to 157B.
*Berry flesh texture*.—Smooth, juicy.
*Berry skin*.—Glabrous with slightly waxiness when mature.
*Berry firmness*.—Firm.
*Berry, particular flavor*.—Fruity, aromatic, juicy.
*Length of pedicel*.—4 mm.
*Pedicel diameter*.—1.5 mm.
*Pedicel color*.—144B.
*Berry, separation from pedicel*.—Difficult.
*Berry, presence of seeds*.—Fully developed.
*Seed number/berry*.—2.
*Seed length*.—6 mm.
*Seed width*.—4 mm.
*Seed length/width ratio*.—Small, 1.5:1.
*Seed weight*.—0.03 g.
*Seed color*.—199A to 199B.

Fruit chemistry: Values represent the means (with ranges in parentheses) for fruit harvested over five growing seasons 2018-2022.
*Harvest date*.—October 15 (October 10-October 20).
*Brix*.—16° (14-18).
*pH*.—3.25 (3.10-3.31).
*Titratable acidity*.—10.95 (10.1-11.8).
*Berry use*.—Wine production.
*Berry storage*.—Not applicable, used directly in wine making when ripe.
*Fruit set*.—High.

Vineyard performance: Based on observations compiled over five years (2018-2022).
*Susceptibility to powdery mildew* (*uncinula necator*).—None.
*Susceptibility to downy mildew* (*plasmopara viticola*).—Low.
*Susceptibility to black rot* (*guignardia bidwellii*).—None.
*Susceptibility to grey mold* (*botrytis cinerea*).—None.
*Susceptibility to foliar phylloxera* (*daktulosphaira vitifoliae*).—None.

*Susceptibility to crown gall* (*agrobacterium tumefaciens*).—Low.

*Susceptibility to phenoxy herbicide drift* (*e.g.*, 2,4-*d*).—None present in Vineyard.

*Pests*.—No susceptibility or resistance has been observed.

*Berry splitting*.—None.

*Berry shelling*.—None.

*Vigor level*.—High.

*Winter hardiness*.—High.

*Wood ripening*.—Good.

It is claimed:

1. A new and distinct cultivar of Grapevine plant named 'Juneau blanc' as herein illustrated and described.

* * * * *